(12) United States Patent
Heinz et al.

(10) Patent No.: US 7,374,555 B2
(45) Date of Patent: May 20, 2008

(54) TAMPER-EVIDENT CLOSURE FOR A SYRINGE

(75) Inventors: Jochen Heinz, Kiel (DE); Alexander Rolle, Schillsdorf (DE); Dieter Schilling, Aukrug-Innien (DE)

(73) Assignee: Transcoject Gesellschaft für medizinische Geräte mbH & Co. KG, Neumuenster (DE)

( * ) Notice: Subject to any disclaimer, the term of this patent is extended or adjusted under 35 U.S.C. 154(b) by 686 days.

(21) Appl. No.: 10/685,008

(22) Filed: Oct. 14, 2003

(65) Prior Publication Data

US 2004/0116858 A1 Jun. 17, 2004

(30) Foreign Application Priority Data

Oct. 15, 2002 (DE) ................ 102 47 965

(51) Int. Cl.
*A61M 5/00* (2006.01)
*A61M 5/31* (2006.01)
*A61M 5/32* (2006.01)

(52) U.S. Cl. .............. 604/111; 604/192; 604/240; 604/256

(58) Field of Classification Search ......... 604/111, 604/93.01, 110, 195, 198, 263, 240–243, 604/192, 256
See application file for complete search history.

(56) References Cited

U.S. PATENT DOCUMENTS

| | | | |
|---|---|---|---|
| 4,220,151 A | * | 9/1980 | Whitney ............. 604/110 |
| 5,135,496 A | | 8/1992 | Vetter et al. |
| 5,506,015 A | | 4/1996 | Frederiksen et al. |
| 5,785,691 A | | 7/1998 | Vetter et al. |
| 5,830,193 A | | 11/1998 | Higashikawa |
| 5,989,227 A | | 11/1999 | Vetter et al. |
| 6,196,998 B1 | | 3/2001 | Jansen et al. |
| 6,280,418 B1 | * | 8/2001 | Reinhard et al. ........ 604/187 |
| 6,520,935 B1 | * | 2/2003 | Jansen et al. ........... 604/111 |

FOREIGN PATENT DOCUMENTS

| DE | 44 34 644 | 8/1997 |
|---|---|---|
| WO | WO 96/32441 | 10/1996 |

OTHER PUBLICATIONS

Search Report dated Oct. 29, 2003 issued for the corresponding European Patent Application No. EP 03 02 1967.

* cited by examiner

*Primary Examiner*—Matthew F. DeSanto
(74) *Attorney, Agent, or Firm*—McGlew and Tuttle P.C.

(57) ABSTRACT

The tamper-evident closure is provided for a syringe with a Luer connection or a Luer lock connection, wherein at least the connection end consists of plastic. A cap which is connected to the syringe via at least one frangible web. The cap and the frangible web together with a fixation component are formed as one piece as a plastic injection molded part and are connected to the connection end of the syringe by way of welding.

9 Claims, 3 Drawing Sheets

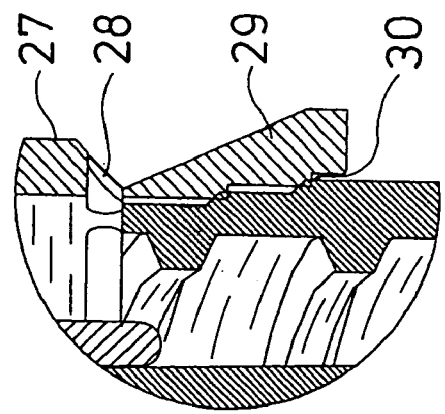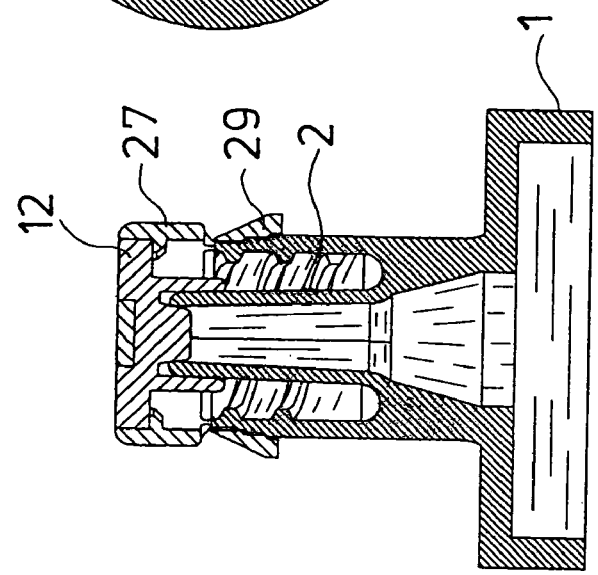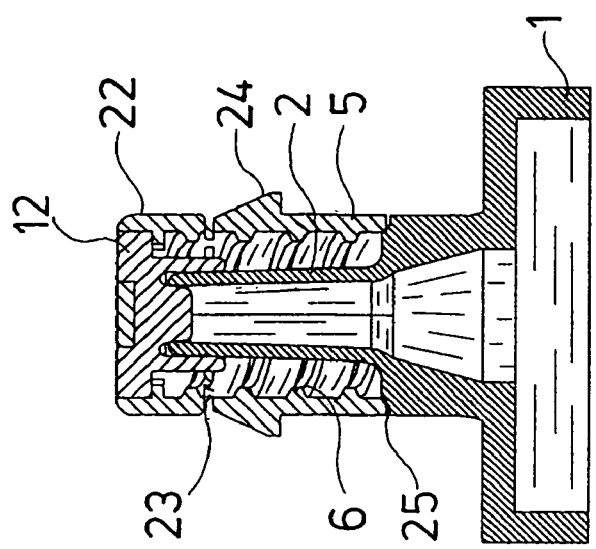

TAMPER-EVIDENT CLOSURE FOR A SYRINGE

BACKGROUND OF THE INVENTION

1. Field of the Invention

The invention relates to a tamper-evident closure for a syringe having a plastic connection end with a Luer connection and a cap and a frangible web formed as a single injection molded part, wherein the cap is fitted to the Luer connection.

2. Description of the Related Art

With syringes, in particular prefilled syringes, one provides a tamper-evident closure which ensures the integrity for the user, i.e. the integrity of the closure and thus of the medium filled into the syringe. Such tamper-evident closures are counted as belong to the state of the art and are known for example from U.S. Pat. No. 5,135,496. This document discloses a glass cylinder on whose end there is attached a component consisting of plastic which comprises a Luer connection onto which later the cannula is placed in a manner known per se, or via which the syringe is connected in another manner. This Luer connection is sealingly closed with a plug which completely encompasses the free end on the inside and well as on the outside. This plug is held by a plastic cap which is connected via a frangible web to a ring as a fixation component. This ring comprises a projection which engages into a corresponding recess at the connection-side end of the syringe and firmly holds this here. With this, the cap, the frangible web and the ring are typically formed as one piece as an injection molded part and are pushed over the connection-side end of the syringe until the projection locks on the ring at the connection-side end.

The problem with such tamper-evident closures which are pushed onto the connection-side end of the syringe in a locking manner is that the manufacturing tolerances are relatively tight in order to ensure that on removal of the cap it is indeed the frangible web that breaks and not the connection between the fixation ring and the connection-side end of the syringe. Then specifically the closure may be placed on again without further ado without the integrity and thus the sterility of the product being guaranteed. There further exists the danger that the frangible web breaks by way of buckling or overstretching already when being placed on. Moreover the frangible web is often designed so solid that a removal of the cap by exerting tension forces alone is not sufficient, and that rather the cap is additionally rotated with respect to the fixation ring by way of hand force. However both hands are then required, one for gripping the fixation ring and the other for gripping the cap. Disregarding the fact that this is awkward, with the medical syringes being discussed here there particularly exists the danger that germs may get into this region by way of this. A thinner dimensioning of the frangible web is often not at all possible or only very difficult to realize with regard to tooling technology since specifically the fixation ring during the injection molding procedure as a rule must be filled with plastic via the frangible web, so that for this reason alone a certain minimum cross section needs to be present in order to ensure a complete filling of the fixation ring during the injection molding procedure.

SUMMARY OF THE INVENTION

Against this background it is the object of the present invention to improve a tamper-evident closure of the initially mentioned type to the extent that on the one hand is may be manufactured inexpensively, but that on the other hand is guarantees the integrity of the closure as long its frangible web is intact.

The basic concept of the present invention is to no longer connect the tamper-evident closure to the connection-side end of the syringe by way of a locking connection but rather by way of a material-fit connection or an adhesive bond. Adhering or preferably welding may effect the material-fit connection. At the same time either the frangible web may be directly welded to the connection-side end of the syringe, or less complicated with regard to manufacturing technology, the frangible web in the known manner may be connected to a fixation component which is then connected to the connection end of the syringe by welding. By way of the material-fit connection provided according to the invention which is created only after pushing on the cap, one may create a considerably more durable connection than this was possible with the previously known locking connections. By way of this the components may be manufactured with a greater tolerance which is advantageous with regard to the manufacturing costs. The frangible web may be dimensioned according to the demands so that the opening forces may be set in a targeted manner. The tooling costs may also be reduced by way of this. If the frangible web is welded directly to the connection end of the syringe, it is of no significance for the functioning of the closure whether the frangible web or the weld seam is broken on opening, i.e. on tearing off the cap. Thus other embodiments are also conceivable in which the frangible web is formed by the weld seam itself, i.e. with which the weld seam forms the break-off location.

According to a preferred embodiment variant the cap, the frangible web and the fixation component are formed as one piece as an injection molded part, wherein then the fixation component after placing on the cap is firmly connected to the connection end of the syringe by way of welding. With a suitable design of the fixation component and of the connection end of the syringe, the welding procedure may be carried out in a simple manner, since no particular demands are may with regard to tolerances. By way of a circumferential weld seam one may manufacture such a stable bond between the fixation component and the connection end of the syringe that even with an unfavorable dimensioning of the frangible web it is always ensured that the break-off location is formed by the frangible web and not by other components or the weld seam.

With a syringe with a Luer lock connection, such a ring may for example be welded without further ado on the syringe-side cylinder section which on its inner side carries the thread of the Luer lock connection. A cylinder section in the context of the invention is always to be understood as a hollow cylinder, thus an annular body.

It is particularly advantageous if the annular fixation component is designed tapering towards the free end of the cylinder section, it is thus the case of a cone-shaped ring, since then the component remaining after tearing off the cap is suitable for simplifying the direct pushing of a flexible tube onto the Luer lock connection and sealing the flexible tube with respect to the outer circumference of the Luer lock connection by way of this raised ring. The ring not only then forms the fixation component but also simultaneously improves the application possibilities of the syringe.

It is particularly advantageous with regard to manufacturing technology if the cylinder section of the Luer lock connection itself forms the fixation component. Then specifically the connection-side end of the syringe may be molded without undercuts, thus may be manufactured with a comparatively less complicated tool. This then is particularly advantageous if the injection-side connection is manufactured together with the syringe cylinder as is known with plastic syringes. The weld connection between the cylinder section and the connection-side end of the syringe cylinder not only then connects the fixation component to the syringe cylinder, but also simultaneously serves as a constructive connection between the cylinder section of the Luer lock connection and the syringe cylinder, thus inasmuch as this is concerned, fulfils design measures required anyway.

As already cited above, it is advantageous to design the fixation component for example as a tapering ring in order in this manner to permit a sliding of a flexible tubing as well as a sealing between the flexible tubing and the cylinder section. At the same time this annular fixation component may either be welded on the cylinder of the Luer lock connection or if the cylinder section of the Luer lock connection itself forms the fixation component, may be additionally integrally formed on this.

In order to ensure that the cap detaches from the syringe-side end, i.e. that the frangible web breaks when applying a defined force, as a rule a hand force, it is useful to design this frangible web accordingly. The frangible web is advantageously circumferential, since it then also forms a hermetic closure between the fixation component and the cap. It may also be interrupted so that there are formed a multitude of individual webs in the manner of a perforation. It is however designed uniformly distributed over the circumference so that the cap may be removed from all directions equally simply or easily. The frangible web may also be provided on only one side in order for example to permit a breaking-off at a targeted break-off location.

The weld connection between the fixation component and the connection end of the syringe or between the frangible web and the connection end of the syringe is preferably formed by ultrasonic welding, it may however also be formed by vibration welding, induction welding, adhering or also other suitable methods for achieving a material fit. It is particularly advantageous if the connection end of the syringe together with the syringe cylinder is formed as one piece as a plastic injection molded part since then only a few components and correspondingly little assembly steps are required for the whole syringe.

The cap attached via the fixation ring or directly may, as is know per se, have an integrated elastic plug which sealingly seals the connection end of the syringe. This plug may either be integrated into the cap as a separate component or may be extruded together with the cap as a one-piece component. According to the invention it may however also be envisaged for the comparatively hard-elastic cap material to be used for directly sealing the Luer connection in that when welding on the cap this is shortened in a targeted manner by the melting-on of the material and is thus set under prestress so that the inner side of the cap bears on the end-face of the Luer connection with this prestress force. An elastic material is thus unnecessary for the closure.

The syringe, in particular the syringe cylinder end part is advantageously formed of polyolefins, preferably polypropylene (PP), cyclo-olefin polymers (COP) or other barrier plastics.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

FIG. 5 ditto one embodiment form with which the Luer connection is provided with a conically tapering ring on the outer circumference;

FIG. 6 ditto the embodiment according to FIG. 5 in an alternative construction manner; and FIG. 7 is a detail of FIG. 6 in an enlarged representation.

DETAILED DESCRIPTION OF THE PRESENTLY PREFERRED EMBODIMENTS

Figure 1:
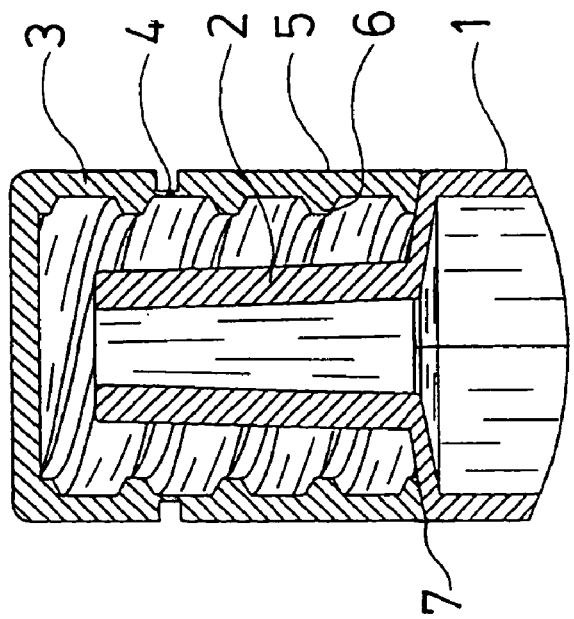
FIG. 1 is a schematic longitudinal section through the connection-side end of a syringe cylinder with a Luer lock connection and cap as a tamper-evident security.

In FIG. 1 there is shown the connection end of a syringe cylinder, which opens into a Luer connection 2 which in a manner known per se is provided for placing on a cannula. The Luer connection 2 and the syringe cylinder 1 are formed as one piece as a plastic injection molded part.

A cap 3 covering the Luer connection 2 at the free end is provided as a tamper-evident closure, which via a circumferential frangible web 4 is connected to a cylinder section 5 which on its inner side comprises a thread 6 and surrounding the Luer connection 2 connects to the connection-side end of the syringe cylinder 1. The cap 3, the frangible web 4 and the cylinder section 5 are likewise formed as one piece as a plastic injection molded part. The cylinder section 5 at its end face facing the syringe cylinder 1 is firmly connected to this cylinder with a material fit by ultrasonic welding to form a weld seam 7.

The tamper-evident closure which is formed in this manner is provided for a syringe which is not prefilled or for a syringe filled with pasty substances. For opening the closure, the cap 3 is removed from the cylinder section 5 by way of hand force, wherein the frangible web 4 is broken. The arrangement and design of the cylinder section 5 with regard to the Luer connection 2 is selected such that a Luer lock connection is formed after removal of the cap 3.

Figure 2:
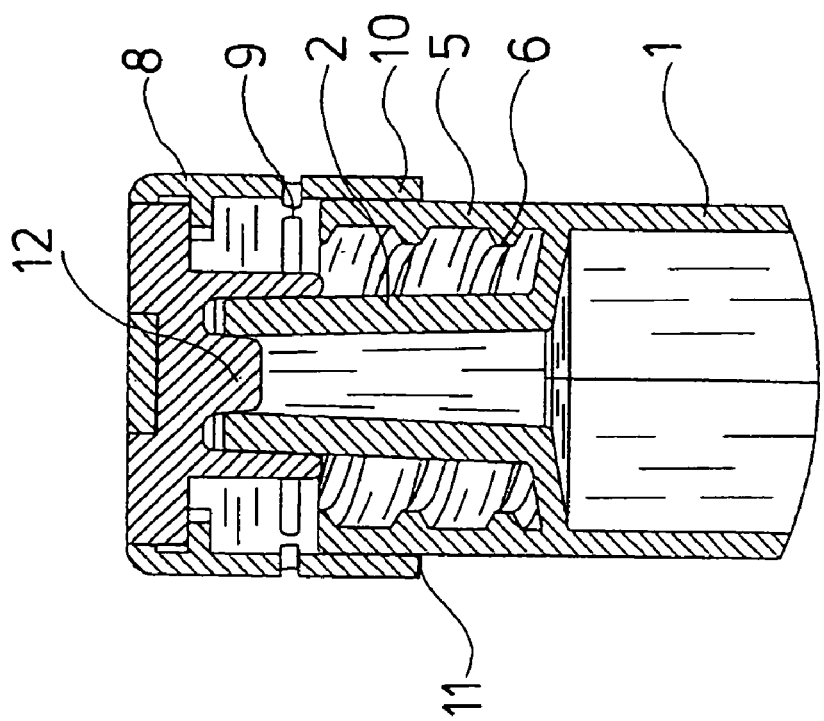
FIG. 2 is a schematic longitudinal section of an alternative embodiment.

With the embodiment variant shown by way of FIG. 2 at the connection end of the syringe cylinder 1 there is formed a complete Luer lock connection consisting of the inner Luer connection 2 and a cylinder section 5 integrally formed with an inner thread 6. With this embodiment there is provided a cap 8 which via a frangible web 9 which is interrupted in sections, is connected to a fixation component 19 in the form of a ring. The ring 10 engages over the end section of the cylinder section 5 of the Luer lock connection on the outer circumference. The components are firmly connected to one another in the overlapping region by ultrasound welding. The weld seam is indicated at 11.

Within the cap 8 there is incorporated a plug 12 which encompasses the Luer connection on the inside of the open end as well as on the outside and sealingly closes this. The plug 12 is formed of a soft-elastic material, whereas the cap 8, the frangible web 9 and the ring 10 are formed of a harder plastic just as the syringe cylinder with the Luer lock connection integrally formed thereon.

The design according to FIG. 2 is particularly suitable for a prefilled syringe. For opening, the cap 8 is pulled from the connection-side end of the syringe, by which means the frangible web 9 or the plurality of frangible webs distributed over the circumference tear, and may be removed together with the plug 12.

Figure 3:
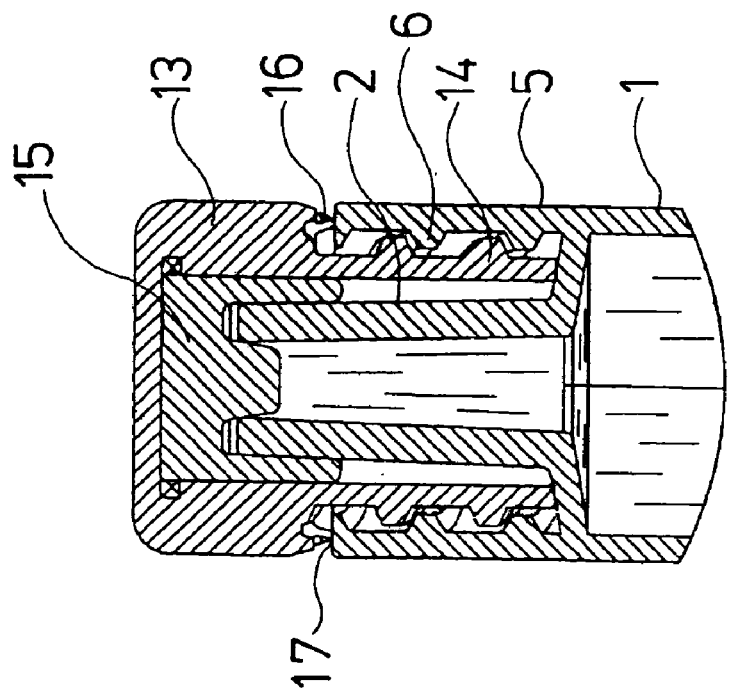
FIG. 3 ditto one embodiment variant with which the frangible web is connected to the connection-side end of the syringe by welding.

With the embodiment according to FIG. 3 the connection-side end of the syringe cylinder 1 is designed in the same manner as that according to FIG. 2. The cap however has a cylinder section 14 with an outer thread which meshes into the inner thread 6 of the cylinder section 5 of the Luer lock connection and thus holds the cap with a positive fit. The cap 13 on its inner side likewise comprises a plug 15 which is provided for the sealed closure of the Luer connection 2. The tamper-evident closure here is formed by a circumferential frangible web 16 which extends from the end-face outer edge of the cap 13 to the end-face end of the cylinder section 5 where it is connected to this with a material fit by way of ultrasonic welding. With this embodiment form the cap 13 and the frangible web 16 are designed as one piece as a plastic injection molded part. For opening the originality closure, the cap 13 is rotated out of the Luer lock thread, wherein the frangible web 16 tears.

Figure 4:
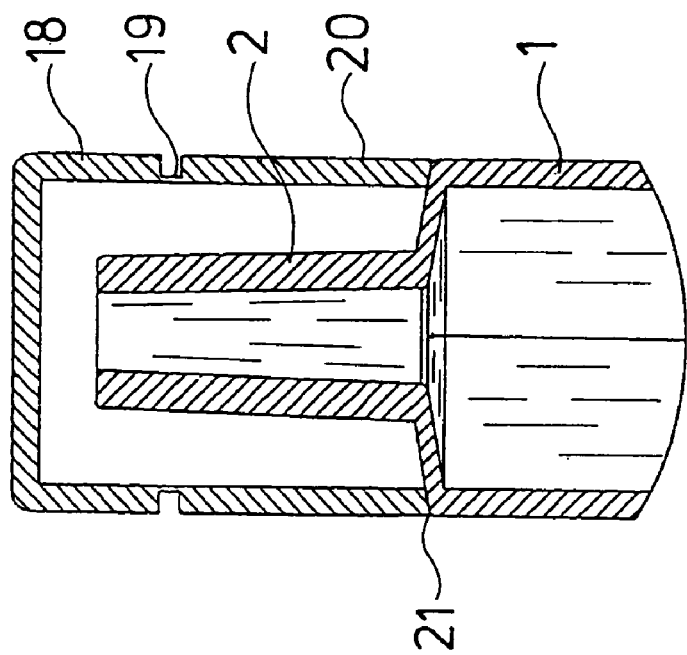
FIG. 4 ditto an embodiment example for a syringe with a Luer connection.

The embodiment according to FIG. 4 shows a tamper-evident closure for a syringe which is not prefilled, with a syringe cylinder 1 with a Luer connection 2. A cup-like cap 18 via a circumferential frangible web 19 is formed as one piece as a plastic injection molded part with a fixation component in the form of a cylinder section. The fixation component 20 is connected at the end face to the syringe cylinder 1 by welding in a manner similar to the embodiment according to FIG. 1 to forma a weld seam 21. The cap 18 is separated from the fixation component 20 by hand force, wherein the frangible web 19 is destroyed and the end of the Luer connection 2 becomes accessible.

The connection-side end of a syringe cylinder 1 represented by way of FIG. 5 opens into a Luer connection 2 and is formed with this as one piece. A cap 22, similar to that described by way of FIG. 2, via an interrupted frangible web 23 is connected to a cylinder section 5 with an inner thread 6 which is part of the Luer lock connection arising after removal of the cap 22. On the outer circumference of the cylinder section 5 near to its free end there is integrally formed a ring 24 which tapers in cross section and which together with the cylinder section 5, the frangible web 23 and the cap 22 is designed as an injection molded part. With this embodiment form too the cap 22 comprises a plug 12 which serves for the sealed closure of the Luer connection 2. The connection of the cylinder section 5 to the connection end of the syringe cylinder 1 is effected via an end-face weld seam 25 similar to the embodiment described by way of FIG. 1.

Here too by way of the force of the hand, the cap 22 with the plug incorporated therein is removed, after the frangible web 23 as a break-off location has been torn from the cylinder section 5. The conically tapering ring 24 enables a flexible tubing to be pushed directly onto the outer circumference of the Luer lock connection. This ring simplifies the pushing-on, the edge formed in the rear region which may also be formed as an annular section or rounding, effects an increases surface pressing between the inner side of the flexible tubing and the outer side of the ring, by which means a sealing effect is achieved.

The embodiment variant shown by way of FIGS. 6 and 7 differs from the one described previously in the fact that in this case the connection end of the syringe cylinder 1 is formed as one piece with a Luer lock connection. The cap 27 via a frangible web 28 which extends over the whole end-face circumference but which however is interrupted in sections, is connected to a fixation component and formed as one piece with this as an injection molded part, which as can be deduced from FIG. 7 has essentially the shape of the conical ring 24. With this embodiment the fixation component is fastened on the outer circumference of the cylinder section 5 by welding to form a weld seam 30. The fixation component 29, after the cap 27 has been removed by breaking the frangible web 28, has the same function as the conical ring 24 described by way of FIG. 5.

As the above embodiment examples illustrate, the present invention apart from a functionally safe tamper-evident closure may also include further functions, which in particular in combination are able to be manufactured more favorably. It is to be understood that the previously described individual features are only to be described by way of example and thus, inasmuch as it is useful, may be practically infinitely combined with one another. Thus for example the embodiment examples represented without a plug may also be manufactured with one, or vice versa. Common to all is the fact that on account of the material-fit, firm weld connection one reliably ensures that on removal of the cap, the frangible web is always detached and not the fixation component (as with the state of the art). In this manner the tamper-evident closure is reliably destroyed after removal of the cap.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A tamper-evident closure for a syringe, said closure comprising:
   a plastic material syringe cylinder having a plastic material connection end provided with a Luer connection; and
   a one piece cap, a frangible web and cylindrical section fixation component formed as a single injection molded plastic part, said cap engaging over at least said Luer connection, said frangible web being connected to said plastic material connection end via said fixation component and said fixation component being connected to said plastic material connection end by a weld connection in which said fixation component is directly welded to said plastic material connection end, preventing relative rotation between said single injection molded plastic part and said plastic material connection end.

2. A tamper-evident closure as in claim 1 wherein said connection end comprises a cylinder section having an internal thread surrounding said Luer connection, said fixation component comprising a ring.

3. A tamper-evident closure as in claim 2 wherein said ring tapers toward a free end of said cylinder section.

4. A tamper-evident closure as in claim 1 wherein said cap is constructed of two different plastics and comprises a plug which is made one plastic which is softer than the other plastic.

5. A tamper-evident closure as in claim 4 wherein said cap including said plug is molded in one piece.

6. A tamper-evident closure as in claim 1 wherein said syringe cylinder, said cap, and said frangible web consist of polyolefins.

7. A tamper-evident closure as in claim 6 wherein said polyolefins are one of polypropylene and cyclo-olefins polymers.

8. A tamper-evident closure as in 1 wherein said frangible web has uniformly spaced circumferential interruptions.

9. A tamper-evident closure as in claim 1 wherein said cap is formed with a predefined prestress which seals said Luer connection.

* * * * *